US012784221B2

(12) United States Patent
Fukuda

(10) Patent No.: US 12,784,221 B2
(45) Date of Patent: Nov. 3, 2026

(54) IMAGE PROCESSING APPARATUS, RADIOGRAPHY SYSTEM, AND PROGRAM

(71) Applicant: FUJIFILM CORPORATION, Tokyo (JP)

(72) Inventor: Wataru Fukuda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 193 days.

(21) Appl. No.: 18/820,274

(22) Filed: Aug. 30, 2024

(65) Prior Publication Data

US 2025/0086796 A1 Mar. 13, 2025

(30) Foreign Application Priority Data

Sep. 12, 2023 (JP) ................................ 2023-147944

(51) Int. Cl.
*G06T 7/00* (2017.01)
*A61B 6/00* (2006.01)
(Continued)

(52) U.S. Cl.
CPC .............. *G06T 7/0014* (2013.01); *A61B 6/03* (2013.01); *A61B 6/0435* (2013.01); *A61B 6/502* (2013.01);
(Continued)

(58) Field of Classification Search
CPC .................. G06T 7/0014; G06T 12/00; G06T 2207/10081; G06T 2207/20084;
(Continued)

(56) References Cited

U.S. PATENT DOCUMENTS 11,445,993 B2 * 9/2022 Chui .................... A61B 6/5205
11,961,234 B1 * 4/2024 Frank .................... G06T 7/0012
(Continued)

FOREIGN PATENT DOCUMENTS

CN 104135935 A * 11/2014 ........... G06T 7/0012
JP 2014-128716 A 7/2014
(Continued)

OTHER PUBLICATIONS

Azam Shadi et al., "Mammographic microcalcifications and risk of breast cancer", British Journal of Cancer, Nature Publishing Group UK, London, vol. 125, No. 5, pp. 759-765, XP037551093, Jun. 14, 2021.

(Continued)

*Primary Examiner* — Jose L Couso
(74) *Attorney, Agent, or Firm* — SOLARIS Intellectual Property Group, PLLC

(57) ABSTRACT

An image processing apparatus includes at least one processor that is configured to: acquire projection images obtained by imaging a subject with radiation at a plurality of angles; reconstruct a plurality of tomographic images from the acquired projection images; detect a plurality of structures of interest from the plurality of reconstructed tomographic images; and determine a priority for each of the structures of interest having the same type among the plurality of detected structures of interest by using a mutual relationship with other structures of interest.

10 Claims, 9 Drawing Sheets

(51) Int. Cl.

| | |
|---|---|
| ***A61B 6/03*** | (2006.01) |
| ***A61B 6/04*** | (2006.01) |
| ***A61B 6/50*** | (2024.01) |
| ***G06T 12/00*** | (2026.01) |
| ***G06V 10/75*** | (2022.01) |

(52) U.S. Cl.
CPC ............ *A61B 6/5217* (2013.01); *G06T 12/00* (2026.01); *G06V 10/751* (2022.01); *G06T 2207/10081* (2013.01); *G06T 2207/20084* (2013.01); *G06T 2207/30068* (2013.01); *G06T 2210/41* (2013.01); *G06T 2211/441* (2023.08); *G06V 2201/03* (2022.01)

(58) Field of Classification Search
CPC ....... G06T 2207/30068; G06T 2210/41; G06T 2211/441; G06T 12/30; G06T 2207/10072; G06T 2207/10116; G06T 7/0012; G06T 11/60; G06T 2207/30004; G06T 2207/30016; G06T 2207/30096; G06T 2207/30101; G06T 3/4046; G06T 5/60; G06T 9/002; G06T 2207/20076; G06T 2207/20081; A61B 6/03; A61B 6/0435; A61B 6/502; A61B 6/5217; A61B 6/025; A61B 6/0036; A61B 6/004; A61B 6/52; G06V 10/751; G06V 2201/03; G06V 10/87; G06V 10/987; G06V 10/454; G06V 10/54; G06V 10/70; G06V 10/7764; G06V 10/774; G06V 10/82; G06V 10/84; G06V 20/41; G06V 30/18057; G06V 20/698; G06V 30/19173; G06V 30/194; G16H 30/20; G16H 30/40; G16H 50/20; G16H 50/70; G06N 3/02; G06N 3/08–088; G06N 3/04; G06N 3/0445; G06N 3/0454; G06N 3/0464; G06N 3/4046; G06N 3/4053; G06N 3/049; G06N 3/0499; G06N 7/00; G06N 7/01; G06N 20/00; G06K 7/1482; G06F 18/213; G06F 18/214; G06F 18/22; G06F 18/241; G06F 18/24; G06F 18/2411; G06F 18/2415; G06F 18/253; G06F 30/27; Y10S 128/925
See application file for complete search history.

(56) References Cited

U.S. PATENT DOCUMENTS

| | | | | |
|---|---|---|---|---|
| 2007/0116347 | A1* | 5/2007 | Hong ...................... | G06T 7/143 382/173 |
| 2009/0123052 | A1 | 5/2009 | Ruth et al. | |
| 2016/0367210 | A1* | 12/2016 | Gkanatsios ............ | A61B 6/502 |
| 2019/0228524 | A1* | 7/2019 | Chen ................... | G06F 18/2148 |
| 2020/0359981 | A1* | 11/2020 | Straka ................ | A61B 5/02007 |
| 2021/0365722 | A1* | 11/2021 | Masuda ................ | G06T 7/0012 |
| 2022/0015731 | A1* | 1/2022 | Liu ........................ | A61B 6/025 |
| 2022/0047154 | A1* | 2/2022 | Prior ...................... | A61B 34/30 |

FOREIGN PATENT DOCUMENTS

| | | | | |
|---|---|---|---|---|
| JP | 2015192748 A | * | 11/2015 ............. | A61B 5/489 |
| WO | 2018/183550 A1 | | 10/2018 | |

OTHER PUBLICATIONS

Extended European Search Report dated Dec. 19, 2024, issued in corresponding EP Patent Application No. 24199302.1.

* cited by examiner

IMAGE PROCESSING APPARATUS, RADIOGRAPHY SYSTEM, AND PROGRAM

CROSS-REFERENCE TO RELATED APPLICATION

This application claims priority from Japanese Patent Application No. 2023-147944, filed Sep. 12, 2023, the disclosure of which is incorporated herein by reference in its entirety.

BACKGROUND

Technical Field

The present disclosure relates to an image processing apparatus, a radiography system, and a non-transitory storage medium storing a program.

Related Art

In recent years, in order to promote early detection of breast cancer, image diagnosis using a radiography apparatus (called mammography) that performs imaging of a breast has attracted attention. In addition, in mammography, there has been proposed tomosynthesis imaging of performing imaging by moving a radiation source and irradiating a breast with radiation at a plurality of radiation source positions, and generating tomographic images in which desired tomographic planes are emphasized by reconstructing a plurality of projection images acquired by the imaging. In the tomosynthesis imaging, a plurality of projection images are acquired by imaging the breast at a plurality of radiation source positions by moving a radiation source in parallel with a radiation detector or moving the radiation source to draw a circle or an elliptical arc in accordance with characteristics of an imaging apparatus and a required tomographic image, and the projection images are reconstructed using a back projection method such as a simple back projection method or a filtered back projection method or a sequential reconstruction method. Thereby, a tomographic image is generated.

The tomographic images are generated on a plurality of tomographic planes of the breast, and thus it is possible to separate structures that are overlapped in a depth direction in which the tomographic planes of the breast are lined up. Therefore, it is possible to find an abnormal part such as a lesion that is unlikely to be detected in a two-dimensional image (hereinafter, referred to as a simple two-dimensional image) acquired by simple imaging in the related art, which irradiates a subject with radiation in a predetermined direction.

As a technology using the tomographic images in this way, JP2014-128716A discloses a technology of generating a pseudo two-dimensional image (hereinafter, referred to as a synthesized two-dimensional image) corresponding to a simple two-dimensional image by synthesizing a plurality of tomographic images having different distances (positions in a height direction) from a detection surface of a radiation detector to a radiation source, using an addition method, an averaging method, a maximum intensity projection method, a minimum intensity projection method, or the like, the tomographic images being acquired by tomosynthesis imaging.

Meanwhile, in a case of creating a synthesized two-dimensional image, it is desirable to emphasize the structure of interest as much as possible. However, in a case where the structures of interest overlap with each other, it is difficult to determine priorities of the structures of interest. Depending on the priority, the structure for reference may become thinner or disappear.

For this reason, U.S. Pat. No. 11,445,993B discloses a technology of detecting an object using an independent recognition module for each type of the object (structure of interest). This technology discloses that, in a case where there is a possibility that a first object and a second object overlap with each other, a weight of the object is calculated from a recognition result of a type of the object and a synthesized two-dimensional image is created according to the weight.

Meanwhile, in a case where a plurality of structures of interest are present in the synthesized two-dimensional image, in many cases, the structures of interest to be focused differ depending on the mutual relationship between the plurality of structures of interest. For example, in a case where a plurality of calcifications are present, in many cases, it is more important to focus on calcifications that densely exist than calcifications that exist alone. In addition, in many cases, calcifications that exist along the mammary glands are more important than other calcifications.

On the other hand, in the technology disclosed in U.S. Pat. No. 11,445,993B, it is possible to set the structures of interest to be focused according to the types of the structures of interest. However, since a mutual relationship between the structures of interest is not considered, there is a problem in that it is not possible to determine superiority and inferiority of the structures of interest having the same type in consideration of the mutual relationship.

SUMMARY

The present disclosure has been made in view of the above circumstances, and an object of the present disclosure is to provide an image processing apparatus, a radiography system, and a non-transitory storage medium storing a program capable of determining superiority and inferiority of structures of interest having the same type in consideration of a mutual relationship between the structures of interest.

In order to achieve the above object, according to a first aspect of the present disclosure, there is provided an image processing apparatus comprising: at least one processor, in which the processor is configured to: acquire projection images obtained by imaging a subject with radiation at a plurality of angles; reconstruct a plurality of tomographic images from the acquired projection images; detect a plurality of structures of interest from the plurality of reconstructed tomographic images; and determine a priority for each of the structures of interest having the same type among the plurality of detected structures of interest by using a mutual relationship with other structures of interest.

According to a second aspect of the present disclosure, in the image processing apparatus according to the first aspect, the processor is configured to create a synthesized two-dimensional image of the subject by using the determined priority.

According to a third aspect of the present disclosure, in the image processing apparatus according to the first aspect, the mutual relationship is at least one of a closeness relationship with the other structures of interest in a three-dimensional distance or a size relationship with the other structures of interest.

According to a fourth aspect of the present disclosure, in the image processing apparatus according to the third aspect, the mutual relationship is both the closeness relationship and the size relationship.

According to a fifth aspect of the present disclosure, in the image processing apparatus according to the first aspect, the structure of interest is at least one type of a calcification, a tumor, a spicula, or a mammary gland.

According to a sixth aspect of the present disclosure, in the image processing apparatus according to the first aspect, the processor is configured to detect the structure of interest by using a machine learning model which is obtained by performing machine learning in advance and in which information indicating the tomographic image is set as input information and information indicating the plurality of structures of interest is set as output information.

According to a seventh aspect of the present disclosure, in the image processing apparatus according to the first aspect, the processor is configured to detect the structure of interest by performing pattern matching using a template image of a target structure of interest.

In addition, in order to achieve the above object, according to an eighth aspect of the present disclosure, there is provided a radiography system comprising: the image processing apparatus according to the first aspect; and a mammography apparatus that acquires projection images to be used by the image processing apparatus.

Further, in order to achieve the above object, according to a ninth aspect of the present disclosure, there is provided a non-transitory storage medium storing a program causing a computer to execute an image process, the image processing comprising: acquiring projection images obtained by imaging a subject with radiation at a plurality of angles; reconstructing a plurality of tomographic images from the acquired projection images; detecting a plurality of structures of interest from the plurality of reconstructed tomographic images; and determining a priority for each of the structures of interest having the same type among the plurality of detected structures of interest by using a mutual relationship with other structures of interest.

According to a tenth aspect of the present disclosure, there is provided a method executed by a computer, the method comprising: acquiring projection images obtained by imaging a subject with radiation at a plurality of angles; reconstructing a plurality of tomographic images from the acquired projection images; detecting a plurality of structures of interest from the plurality of reconstructed tomographic images; and determining a priority for each of the structures of interest having the same type among the plurality of detected structures of interest by using a mutual relationship with other structures of interest.

According to the present disclosure, it is possible to determine superiority and inferiority of structures of interest having the same type in consideration of a mutual relationship between the structures of interest.

DETAILED DESCRIPTION

Figure 1:
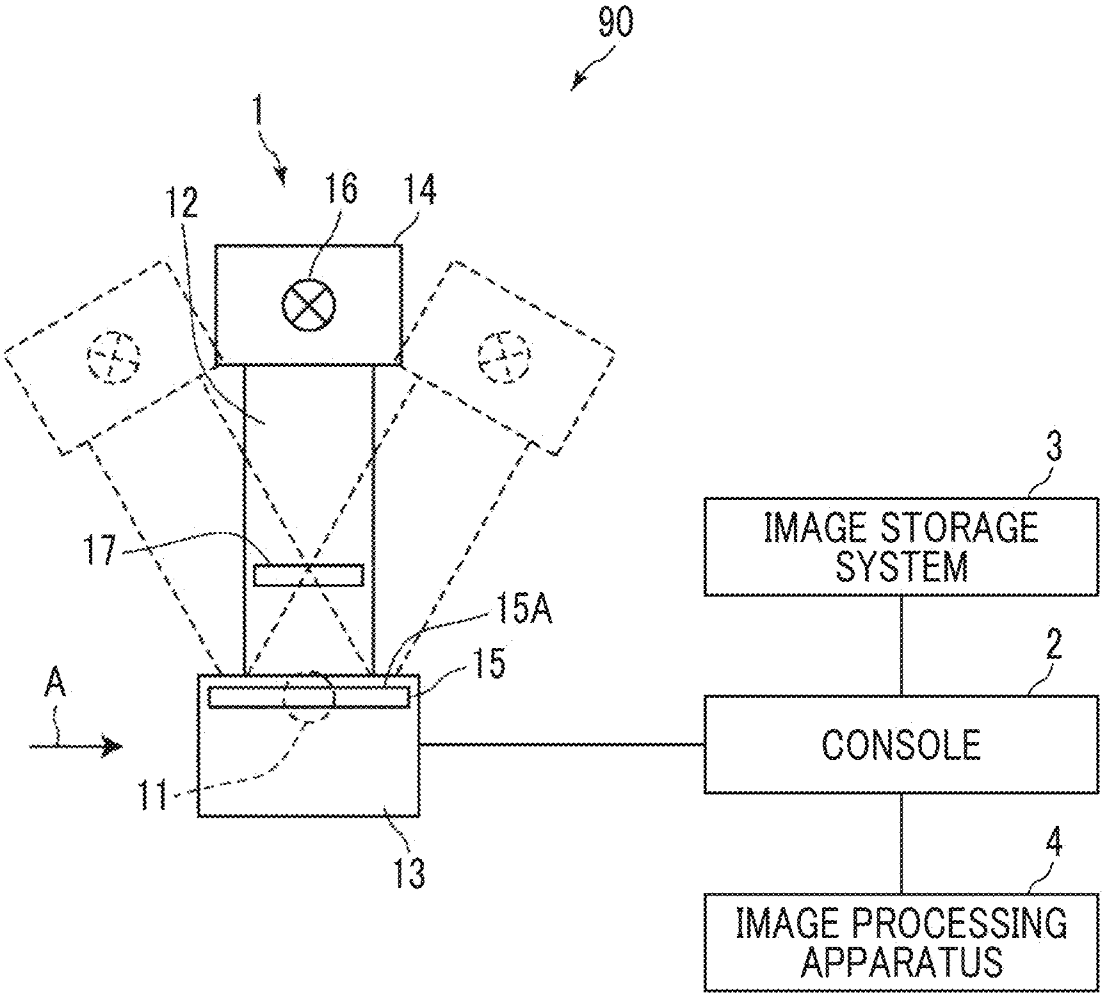
FIG. 1 is a schematic configuration diagram of a radiography system to which an image processing apparatus according to an embodiment is applied.
Figure 2:
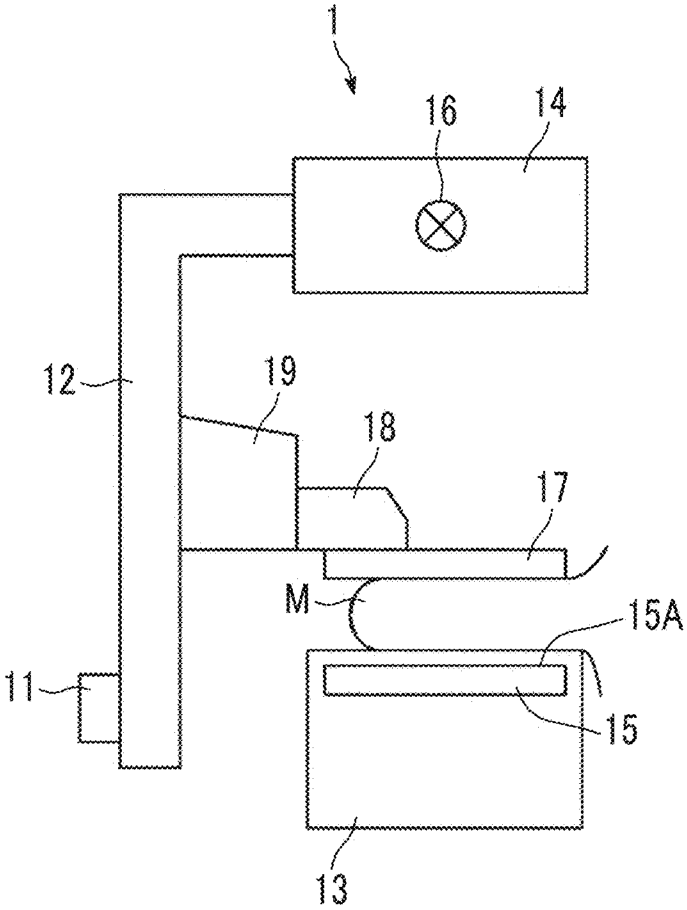
FIG. 2 is a diagram illustrating a mammography apparatus according to the embodiment as viewed from a direction of an arrow A in FIG. 1.

Hereinafter, an embodiment of the present disclosure will be described with reference to the drawings. FIG. 1 is a schematic configuration diagram of a radiography system 90 to which an image processing apparatus 4 according to an embodiment of the present disclosure is applied, and FIG. 2 is a diagram illustrating a mammography apparatus 1 in the radiography system 90 as viewed from a direction of an arrow A in FIG. 1.

As illustrated in FIG. 1, a radiography system 90 according to the present embodiment performs imaging of a breast M, which is a subject, at a plurality of radiation source positions and acquires a plurality of radiation images, that is, a plurality of projection images, in order to perform tomosynthesis imaging on the breast to generate tomographic images. The radiography system 90 according to the present embodiment comprises a mammography apparatus 1, a console 2, an image storage system 3, and an image processing apparatus 4.

The mammography apparatus 1 comprises an arm part 12 that is connected to a base (not illustrated) by a rotation shaft 11. An imaging table 13 is attached to one end of the arm part 12, and a radiation emitting unit 14 is attached to the other end of the arm part 12 so as to face the imaging table 13. The arm part 12 is configured such that only the end to which the radiation emitting unit 14 is attached can be rotated. Therefore, the imaging table 13 is fixed and only the radiation emitting unit 14 can be rotated.

A radiation detector 15, such as a flat panel detector, is provided in the imaging table 13. The radiation detector 15 has a radiation detection surface 15A. In addition, a circuit board including a charge amplifier that converts a charge signal read from the radiation detector 15 into a voltage signal, a sampling two correlation pile circuit that samples the voltage signal output from the charge amplifier, and an analog-to-digital (AD) conversion unit that converts the voltage signal into a digital signal is provided in the imaging table 13.

A radiation source 16 is accommodated in the radiation emitting unit 14. The radiation source 16 emits X-rays as radiation. The console 2 controls a timing when the radiation source 16 emits the radiation and radiation generation conditions of the radiation source 16, that is, selection of a target and filter materials, a tube voltage, an irradiation time, and the like.

Further, the arm part 12 is provided with a compression plate 17 that is disposed above the imaging table 13 and presses and compresses the breast M, a support part 18 that supports the compression plate 17, and a moving mechanism 19 that moves the support part 18 in a vertical direction in FIG. 1 and FIG. 2. A distance between the compression plate 17 and the imaging table 13, that is, a compression thickness is input to the console 2.

The console 2 has a function of controlling the mammography apparatus 1 using, for example, an imaging order and various kinds of information acquired from a radiology information system (RIS) (not illustrated) or the like through a network, such as a wireless communication local area network (LAN), and instructions or the like directly issued by an engineer or the like. Specifically, the console 2 acquires a plurality of projection images as described below by causing the mammography apparatus 1 to perform tomosynthesis imaging of the breast M. As an example, in the present embodiment, a server computer is used as the console 2.

The image storage system 3 is a system that stores image data such as the projection images which are obtained by imaging of the mammography apparatus 1. The image storage system 3 extracts an image corresponding to a request from, for example, the console 2 and the image processing apparatus 4 from the stored images and transmits the image to a device that is the source of the request. A specific example of the image storage system 3 is a picture archiving and communication system (PACS).

Figure 3:
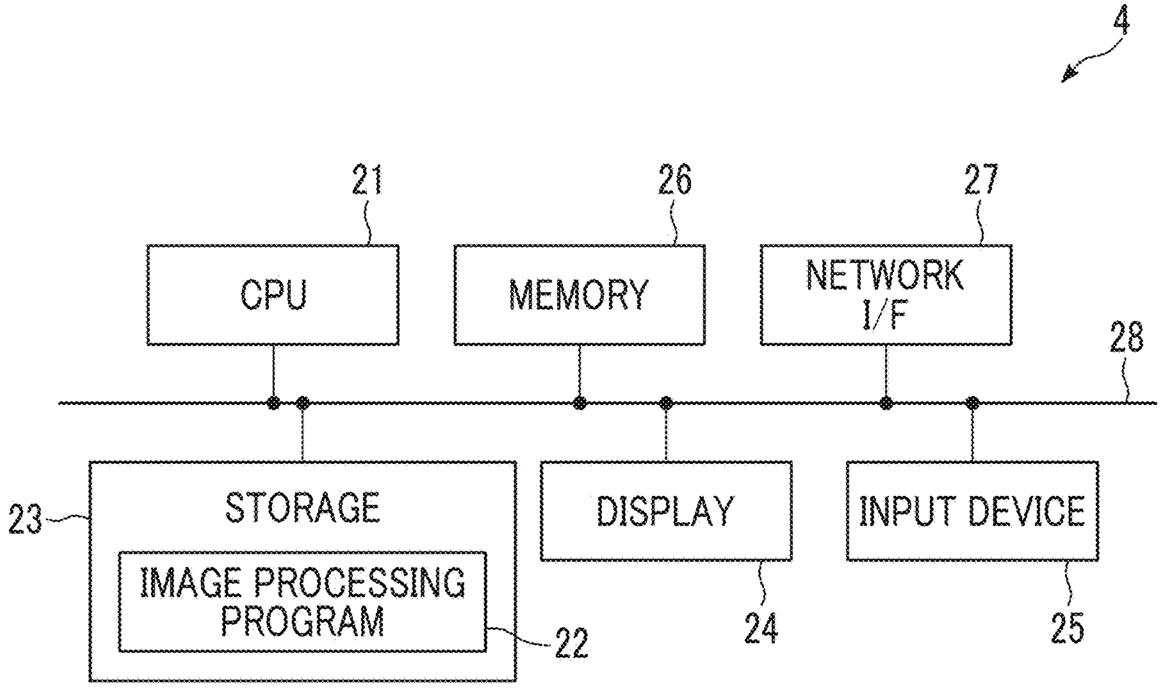
FIG. 3 is a block diagram illustrating an example of an electrical configuration of the image processing apparatus according to the embodiment.

Next, the image processing apparatus 4 according to the present embodiment will be described. Next, a hardware configuration of the image processing apparatus 4 according to the present embodiment will be described with reference to FIG. 3. As illustrated in FIG. 3, the image processing apparatus 4 is a computer, such as a workstation, a server computer, and a personal computer, and comprises a central processing unit (CPU) 21, a non-volatile storage 23, and a memory 26 as a transitory storage region. In addition, the image processing apparatus 4 comprises a display 24 such as a liquid crystal display, an input device 25 such as a keyboard and a mouse, and a network interface (I/F) 27 connected to a network (not illustrated). The CPU 21, the storage 23, the display 24, the input device 25, the memory 26, and the network I/F 27 are connected to a bus 28. In addition, the CPU 21 is an example of a processor according to the present disclosure.

The storage 23 is implemented by a hard disk drive (HDD), a solid state drive (SSD), a flash memory, and the like. An image processing program 22 to be installed in the image processing apparatus 4 is stored in the storage 23 as a storage medium. The CPU 21 reads out the image processing program 22 from the storage 23, expands the image processing program 22 in the memory 26, and executes the expanded image processing program 22.

The image processing program 22 is stored in a storage device of a server computer connected to the network or in a network storage in a state of being accessible from the outside, and is downloaded and installed in the computer that configures the image processing apparatus 4 in response to a request. Alternatively, the image processing program 22 is distributed in a state of being recorded on a recording medium, such as a digital versatile disc (DVD) or a compact disc read only memory (CD-ROM), and is installed in the computer that configures the image processing apparatus 4 from the recording medium.

Figure 4:
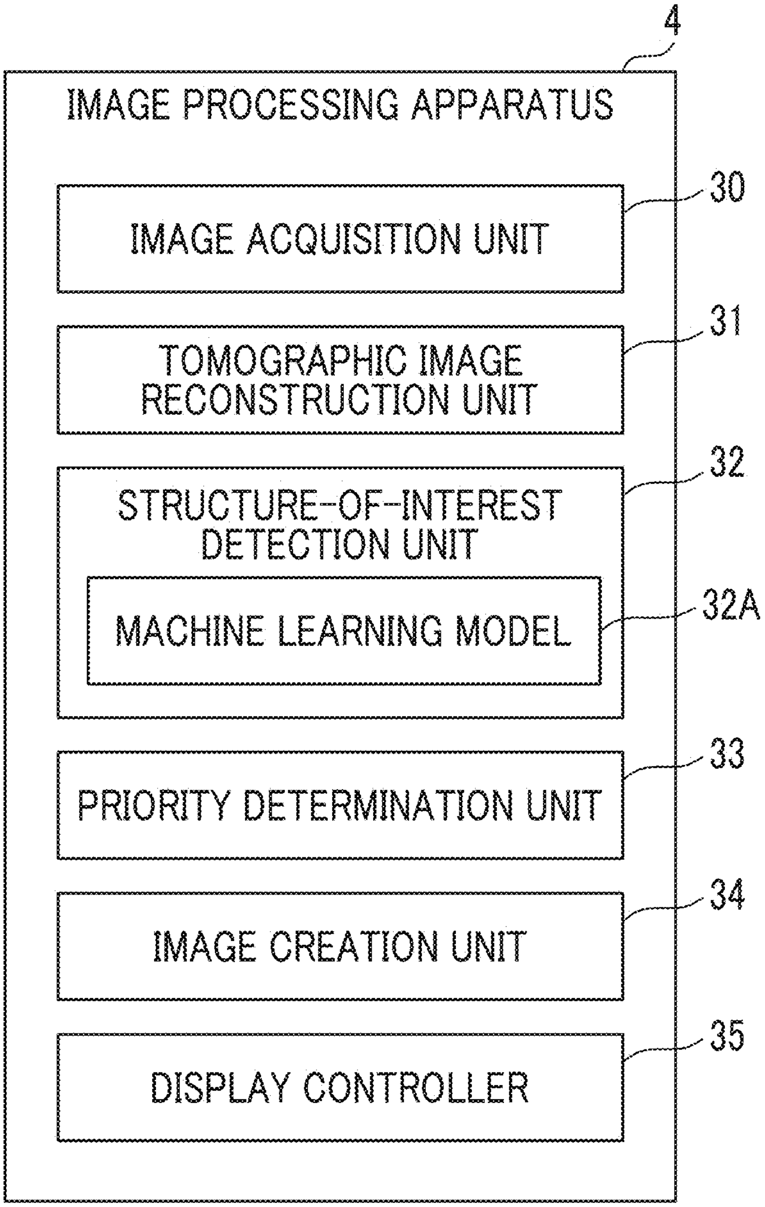
FIG. 4 is a functional block diagram illustrating a functional configuration of the image processing apparatus according to the embodiment.

Hereinafter, a functional configuration of the image processing apparatus 4 according to the present embodiment will be described. FIG. 4 is a diagram illustrating a functional configuration of the image processing apparatus 4 according to the present embodiment.

As illustrated in FIG. 4, the image processing apparatus 4 according to the present embodiment comprises an image acquisition unit 30, a tomographic image reconstruction unit 31, a structure-of-interest detection unit 32, a priority determination unit 33, an image creation unit 34, and a display controller 35. In addition, in a case where the CPU 21 executes the image processing program 22, the image processing apparatus 4 functions as the image acquisition unit 30, the tomographic image reconstruction unit 31, the structure-of-interest detection unit 32, the priority determination unit 33, the image creation unit 34, and the display controller 35.

The image acquisition unit 30 acquires a plurality of projection images acquired by causing the console 2 to perform tomosynthesis imaging on the breast M by the mammography apparatus 1. The image acquisition unit 30 acquires the projection images from the console 2 or the image storage system 3 via the network I/F 27. Further, the tomographic image reconstruction unit 31 reconstructs a plurality of tomographic images from the projection images acquired by the image acquisition unit 30.

Here, the tomosynthesis imaging and the generation of the tomographic image will be described. In a case of performing the tomosynthesis imaging for generating a tomographic image, the console 2 acquires a plurality of projection images Gi (i=1 to n, where n is the number of radiation source positions and is, for example, n=15) at a plurality of radiation source positions by moving the radiation source 16 by rotating the arm part 12 around the rotation shaft 11, irradiating the breast M as a subject with radiation at a plurality of radiation source positions obtained by the movement of the radiation source 16 according to predetermined imaging conditions for tomosynthesis imaging, and detecting the radiation passing through the breast M by the radiation detector 15.

Figure 5:
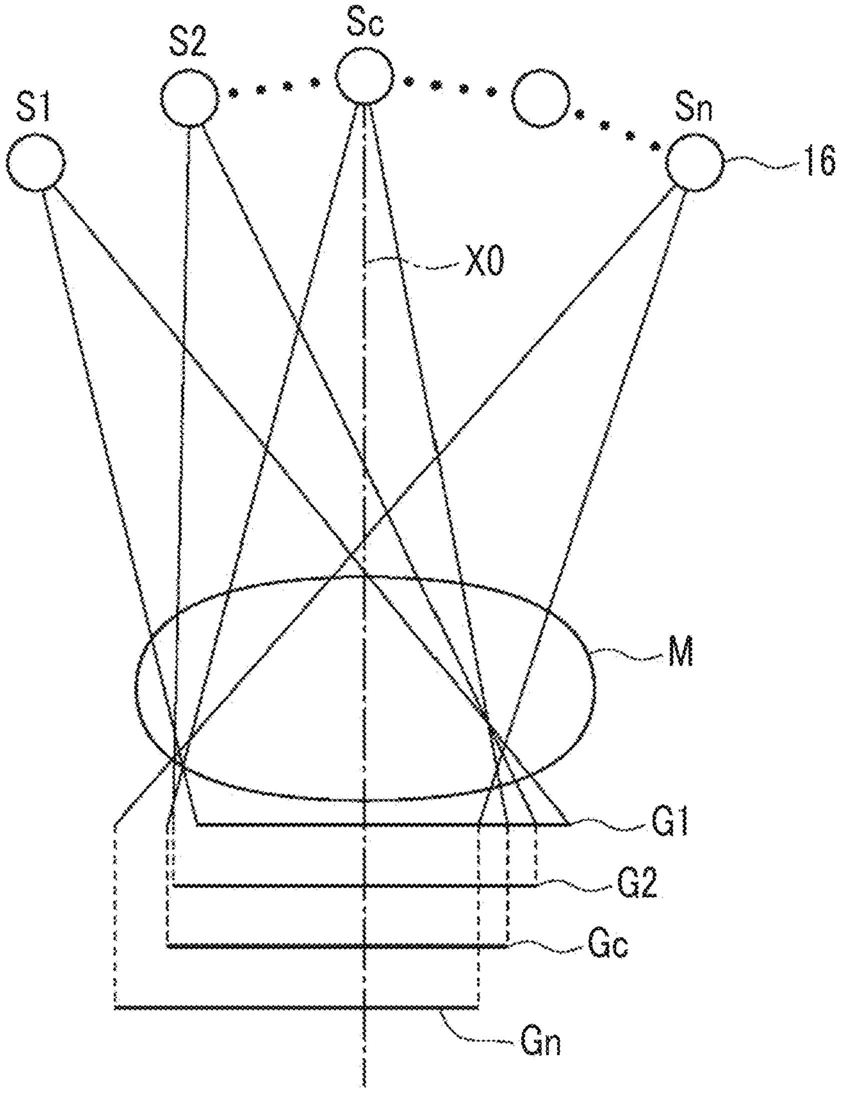
FIG. 5 is a diagram for describing acquisition of projection images according to the embodiment.

FIG. 5 is a diagram for describing the acquisition of the projection images Gi. As illustrated in FIG. 5, the radiation source 16 is moved to each of radiation source positions S1, S2, . . . , and Sn. The radiation source 16 drives and irradiates the breast M with radiation at each of the radiation source positions. The radiation detector 15 detects X-rays passing through the breast M, and thus the projection images G1, G2, . . . , and Gn corresponding to the radiation source positions S1 to Sn are acquired. At each of the radiation source positions S1 to Sn, the breast M is irradiated with the same dose of radiation.

In FIG. 5, the radiation source position Sc is a radiation source position at which the optical axis X0 of the radiation emitted from the radiation source 16 is orthogonal to the detection surface 15A of the radiation detector 15. The radiation source position Se is referred to as a reference radiation source position Sc.

Figure 6:
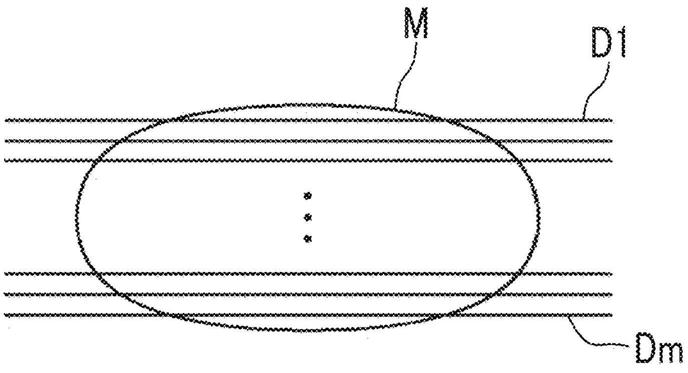
FIG. 6 is a diagram for describing generation of tomographic images according to the embodiment.

In addition, the tomographic image reconstruction unit 31 generates a tomographic image in which the desired tomographic planes of the breast M are emphasized by reconstructing the plurality of projection images Gi. Specifically, the image processing apparatus 4 generates a plurality of tomographic images Dj (j=1 to m) on each of the plurality of tomographic planes of the breast M as illustrated in FIG. 6 by reconstructing the plurality of projection images Gi using a known back projection method, such as a simple back projection method or a filtered back projection method. In this case, a three-dimensional coordinate position in a three-dimensional space including the breast M is set, pixel values of the corresponding pixels in the plurality of projection images Gi are reconstructed with respect to the set three-dimensional coordinate position, and pixel values at the coordinate positions are calculated.

The structure-of-interest detection unit 32 detects a structure of interest from the plurality of tomographic images Dj. In the present embodiment, a calcification, a tumor, a spicula, and a mammary gland included in the breast M are detected as the structure of interest.

The structure-of-interest detection unit 32 according to the present embodiment detects a structure-of-interest by using a machine learning model 32A that is configured with a neural network obtained by performing machine learning, such as deep learning, using training data so as to extract a structure-of-interest from each of the tomographic images Dj. That is, the machine learning model 32A according to the present embodiment is a machine learning model in which information indicating the tomographic image is set as input information, and information indicating a plurality of types of structures of interest is set as output information, and is obtained by performing machine learning in advance.

As the machine learning model 32A, for example, a well-known neural network, such as a convolutional neural network (CNN) or a support vector machine (SVM), can be used.

In the present embodiment, although a single machine learning model 32A that can detect a plurality of types of structures of interest is applied, the present disclosure is not limited thereto. For example, the machine learning model 32A may be prepared and applied for each type of the structures of interest to be detected.

As described above, in the present embodiment, the structure of interest is detected by the machine learning model 32A. On the other hand, the present disclosure is not limited thereto. For example, an aspect in which the structure of interest is detected from the tomographic image Dj using a known computer aided diagnosis (that is, CAD) algorithm may be used. In the algorithm by the CAD, the probability (likelihood) indicating that the pixel in the tomographic image Dj is the structure of interest is derived, and the pixel in which the probability is equal to or higher than the predetermined threshold value is detected as the structure of interest. An algorithm by CAD is prepared for each type of the structures of interest. In a case where the algorithm by the CAD is applied in the present embodiment, a CAD algorithm for tumor detection, a CAD algorithm for spicula detection, a CAD algorithm for calcification detection, and a CAD algorithm for mammary gland detection are prepared.

In addition, the detection of the structure of interest is not limited to detection using the machine learning model 32A or detection using the CAD. For example, the structure of interest may be detected from the tomographic image Dj by performing pattern matching using a template image of a structure of interest to be detected or a filtering process using a filter for detecting the structure of interest. Here, in a case where the pattern matching is applied, an image that is already acquired for the type of the structure of interest to be extracted is applied as the template image.

In addition, in the present embodiment, the structure of interest is detected using only the machine learning model 32A, but the present disclosure is not limited thereto. For example, a form in which the structure of interest is detected by using both the machine learning model 32A and the pattern matching may be used. Further, in this form, a method of detecting the structure of interest may be switched according to the type of the structure of interest to be detected.

As described above, in the present embodiment, all of the calcification, the tumor, the spicula, and the mammary gland are applied as the structures of interest to be detected, but the present disclosure is not limited thereto. For example, a plurality of combinations excluding any one or all of the calcification, the tumor, the spicula, and the mammary gland may be applied as the structures of interest to be detected.

The priority determination unit 33 determines a priority of each of the structures of interest having the same type among the plurality of structures of interest that are detected by the structure-of-interest detection unit 32, by using a mutual relationship with the other structures of interest.

In the present embodiment, as the mutual relationship, both a closeness relationship with the other structures of interest in three-dimensional distance and a size relationship with the other structures of interest are applied, but the present disclosure is not limited thereto. For example, a form in which only one of the closeness relationship or the size relationship is applied as the mutual relationship may be adopted. A method of determining the priority by the priority determination unit 33 will be described in detail below.

The image creation unit 34 creates a synthesized two-dimensional image of the subject (in the present embodiment, the breast M) by using the priority determined by the priority determination unit 33.

The image creation unit 34 according to the present embodiment creates a synthesized two-dimensional image by taking a weighted average for each pixel by setting a weight value (for example, 0.9) of a tomographic image including the structure of interest having a high priority determined by the priority determination unit 33 to a value larger than a weight value (for example, 0.1) of a tomographic image other than the tomographic image. Here, the method of creating the synthesized two-dimensional image is not limited to such an averaging method, and an addition method, a maximum intensity projection method, a minimum intensity projection method, or the like may be applied as a method of creating the synthesized two-dimensional image.

For example, in a case where the minimum intensity projection method is applied as a method of creating the synthesized two-dimensional image, among the tomographic images to be projected, only tomographic images including the structures of interest having a high priority may be projected.

As described above, in the present embodiment, the synthesized two-dimensional image is applied as the image created by the image creation unit 34, but the present disclosure is not limited thereto. For example, a form in which a slab image that is an image including thickness information is applied as the image created by the image creation unit 34 may be adopted. As a form example in this case, a form in which only the tomographic images including the structures of interest having a high priority are used to create the slab images may be used.

The display controller 35 displays the synthesized two-dimensional image generated by the image creation unit 34 on the display 24. The synthesized two-dimensional image is created by setting a weight value for the tomographic image including the structure of interest having a high priority to be larger than weight values for other tomographic images. Therefore, the synthesized two-dimensional image displayed here is an extremely-high-quality image in which the structure of interest having a high priority is emphasized.

The image created by the image creation unit 34 is not limited to the synthesized two-dimensional image and the slab image described above, and may be an image for performing display of linking the synthesized two-dimensional image created from the plurality of tomographic images Dj with the corresponding tomographic images Dj.

That is, in general, the number of the tomographic images may be equal to or larger than 100 depending on the application. Therefore, in a case of reading the tomographic images, there is a problem that a relatively long reading time is required.

Therefore, in this form, the CPU 21 first creates a synthesized two-dimensional image as described above, and displays the synthesized two-dimensional image. Accordingly, an operator refers to the displayed synthesized two-dimensional image, and in a case where a lesion is suspected in the structure of interest displayed on the synthesized two-dimensional image, designates the structure of interest. In response to the designation, the CPU 21 displays the tomographic image including the designated structure of interest. Thereby, a reading time of the tomographic image can be significantly shortened.

Next, a method of determining the priority by the priority determination unit 33 according to the present embodiment will be specifically described with reference to FIG. 7 to FIG. 11. FIG. 7 to FIG. 11 are diagrams for describing the priority determination method according to the present embodiment. Here, a case where three types of structures of interest, that is, a calcification, a tumor, and a spicula are included will be described.

Figure 7:
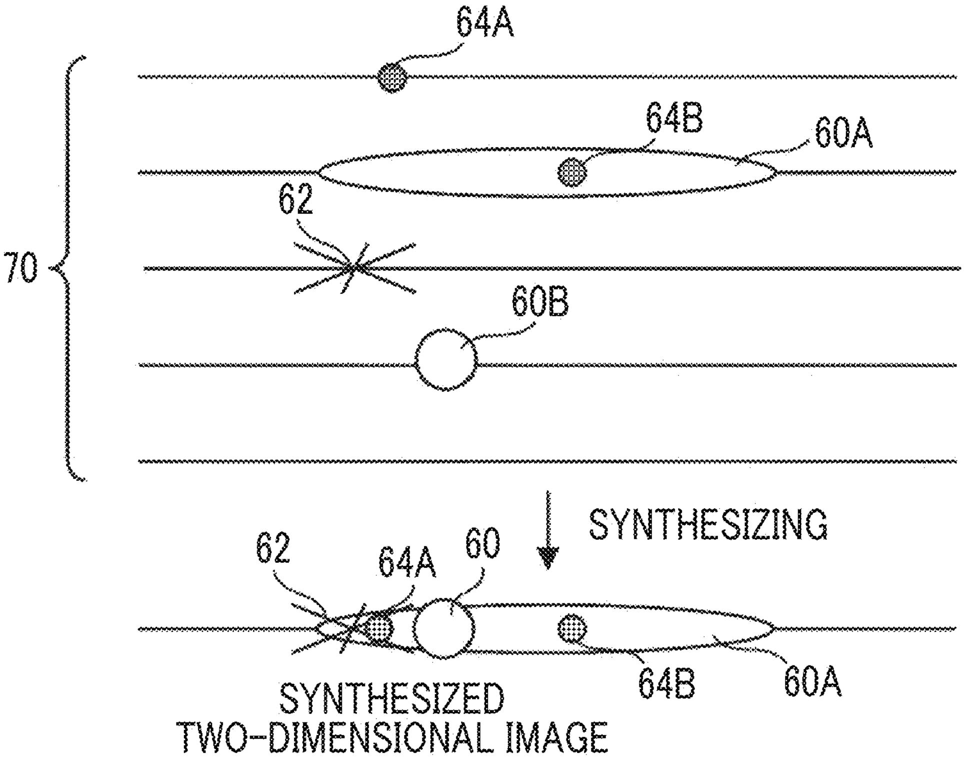
FIG. 7 is a diagram for describing a priority determination method according to the embodiment.

In the example illustrated in FIG. 7 as an example, as illustrated in an upper part of FIG. 7, in the tomographic plane 70 corresponding to each of the tomographic images Dj, the structures of interest corresponding to the tumors 60A and 60B, the spicula 62, and the calcifications 64A and 64B are present in the depth direction in which the tomographic planes are arranged. In a case where it is assumed that the synthesized two-dimensional image created by synthesizing the tomographic images Dj in this state in the depth direction is viewed from the front, a state illustrated in a lower part of FIG. 7, that is, a state where all the structures of interest overlap with each other on a one-dimensional axis is obtained.

Figure 8:
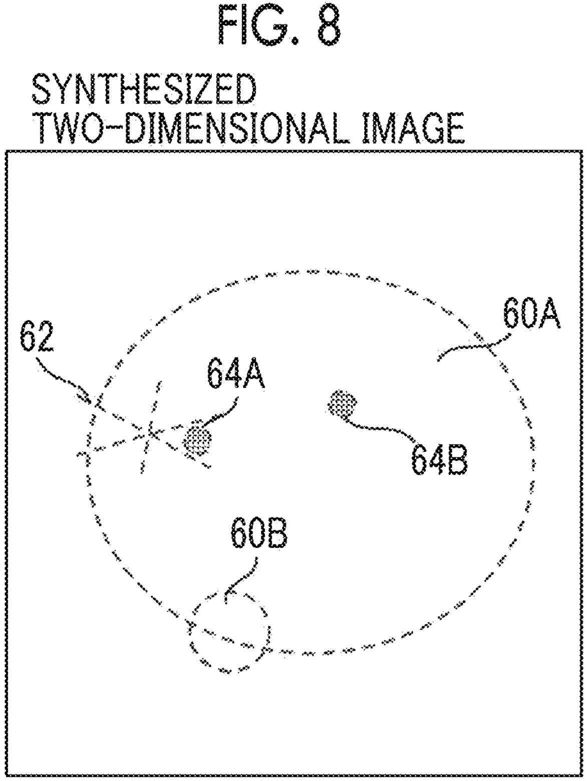
FIG. 8 is a diagram for describing the priority determination method according to the embodiment.

In this state, in a case where the synthesized two-dimensional image is created by synthesizing all of the tomographic images Dj at the same ratio (weight value), as illustrated in FIG. 8 as an example, the densities of all of the structures of interest are averaged and reduced. Thus, the densities of all of the structures of interest become uniform. For this reason, for example, in a state where there are a plurality of structures of interest having the same type, in a case where it is desired to interpret the image while paying attention to some of the structures of interest, it is difficult to distinguish between a structure of interest and the other structures of interest. As a result, there is a problem that it is difficult to interpret the image.

Therefore, as described above, the priority determination unit 33 according to the present embodiment determines, for each of the structures of interest having the same type, the priority of the structures of interest having the same type by using the predetermined closeness relationship and the predetermined size relationship.

Figure 9:
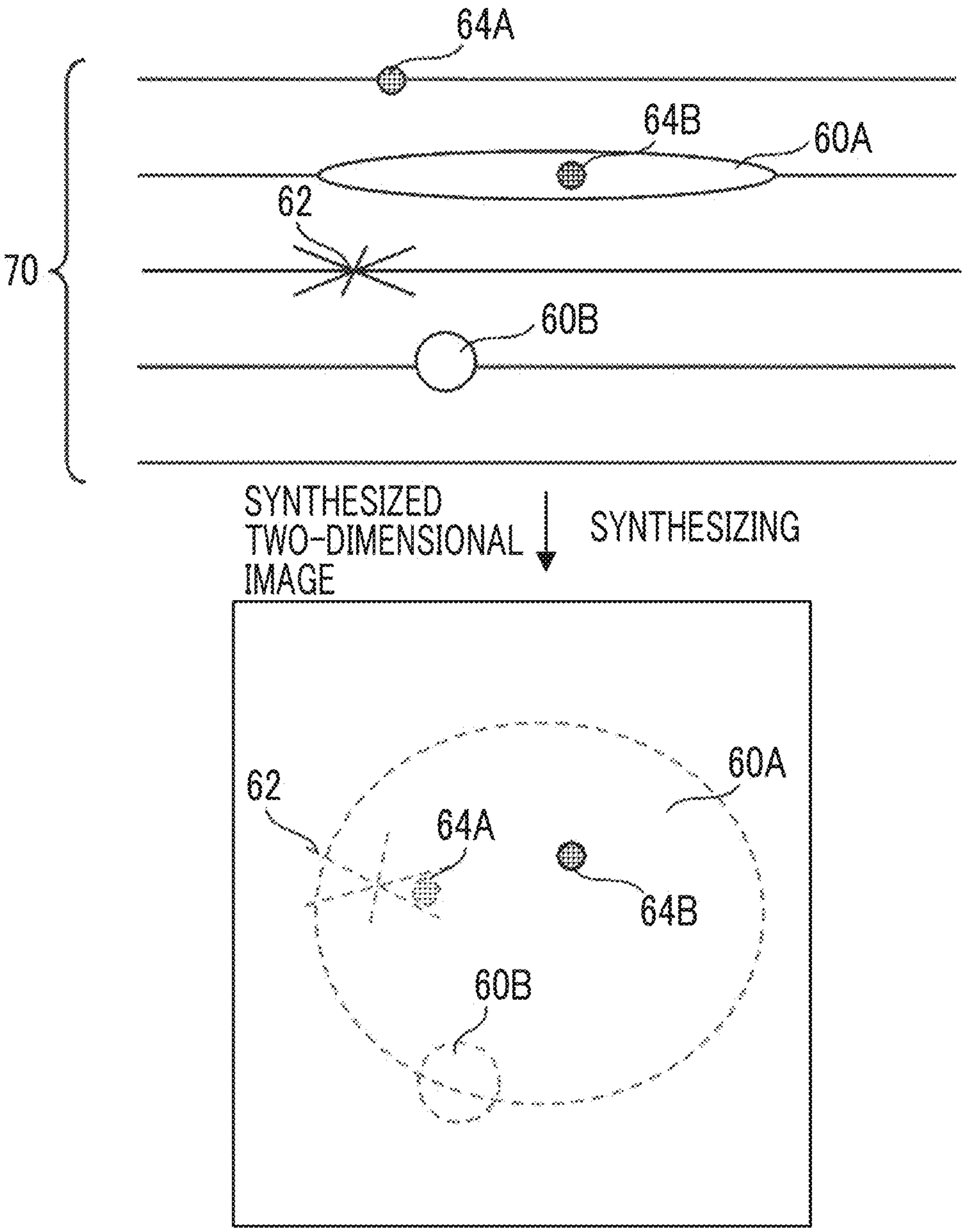
FIG. 9 is a diagram for describing the priority determination method according to the embodiment.

The example illustrated in FIG. 9 is an example in which two tumors 60 (60A and 60B) and two calcifications 64 (64A and 64B) are present and only one spicula 62 is present. In this case, in a case where the operator wants to perform interpretation while paying attention to the calcification 64 and a relationship indicating overlapping with another structure of interest in a three-dimensional space is applied as the closeness relationship, the calcification 64B overlaps with the tumor 60A in the three-dimensional space. Therefore, the priority of the calcification 64B is set to be higher than priorities of the other structures of interest. As a result, as illustrated in a lower part of FIG. 9 as an example, the synthesized two-dimensional image created by using the priority is an image in which only the calcification 64B is emphasized.

Figure 10:
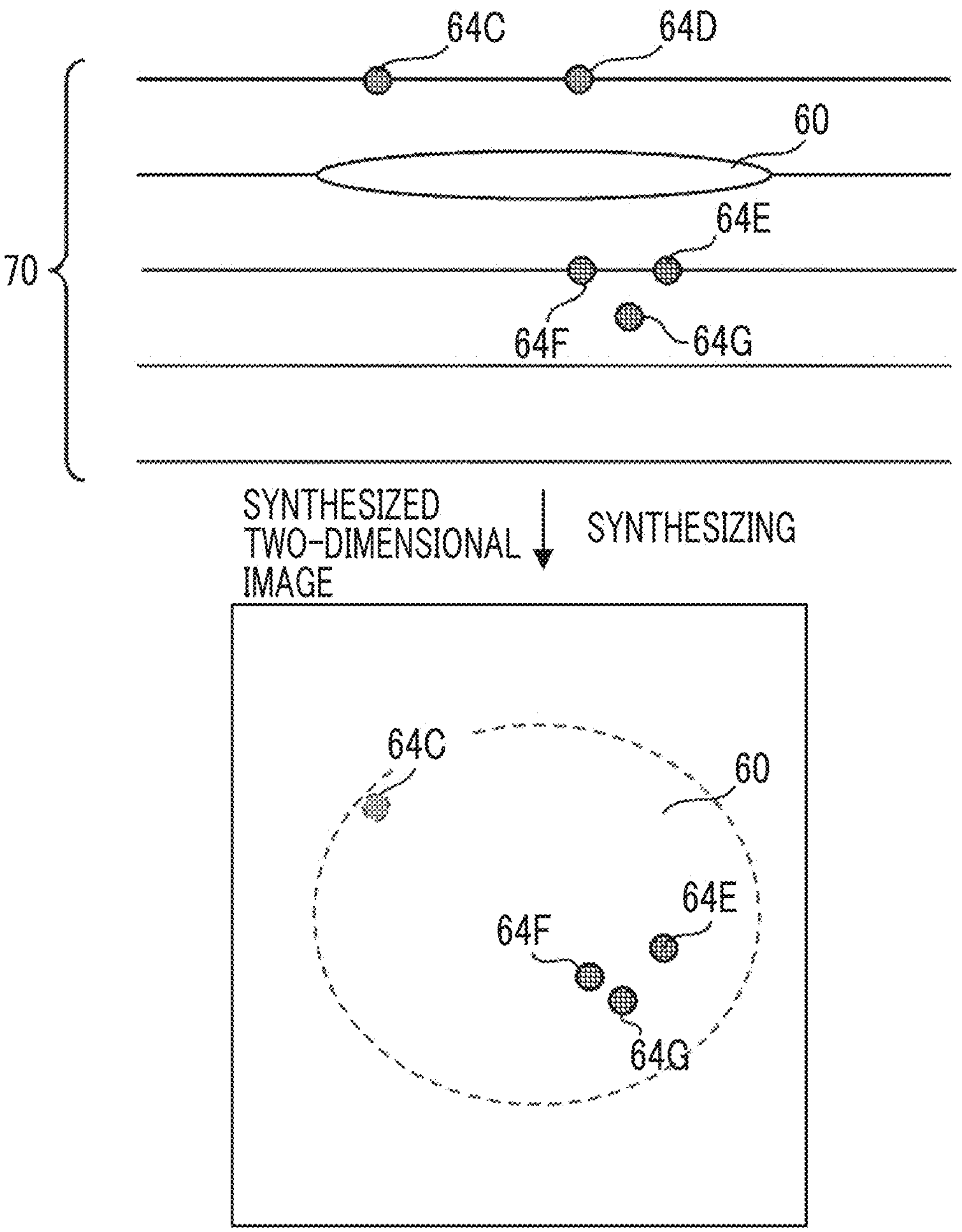
FIG. 10 is a diagram for describing the priority determination method according to the embodiment.

On the other hand, the example illustrated in FIG. 10 is an example in which five calcifications 64 (64C to 64G) are present and only one tumor 60 is present. In this case, in a case where the operator wants to perform interpretation while paying attention to the calcification 64 and a relationship indicating closeness to another structure of interest in a three-dimensional space is applied as the closeness relationship, the calcifications 64E, 64F, and 64G are close to each other in the three-dimensional space. Therefore, the priority of the calcifications 64E, 64F, and 64G is set to be higher than priorities of other structures of interest. As a result, as illustrated in the lower part of FIG. 10 as an example, the synthesized two-dimensional image created by using the priority is an image in which only the calcifications 64E, 64F, and 64G are emphasized.

Figure 11:
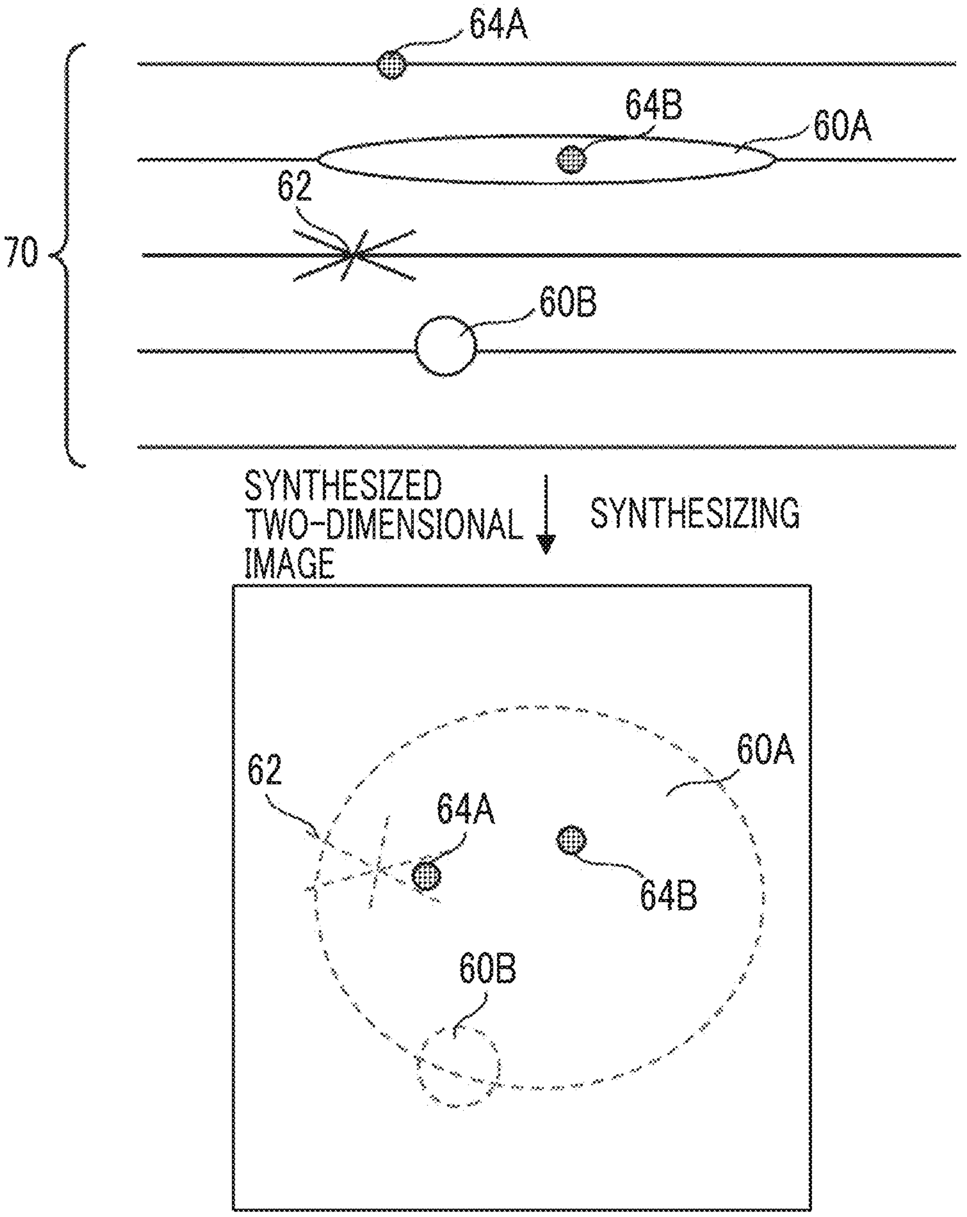
FIG. 11 is a diagram for describing the priority determination method according to the embodiment.

Further, the example illustrated in FIG. 11 is an example in which two tumors 60 (60A and 60B) and two calcifications 64 (64A and 64B) are present and only one spicula 62 is present, which is the same as the example illustrated in FIG. 9. In this case, in a case where the operator wants to perform interpretation while paying attention to the calcification 64 and a relationship indicating smallness with respect to a size of another structure of interest in a three-dimensional space (in the present embodiment, a volume equal to or smaller than 1/10 of the structure of interest having a largest volume) is applied as the relationship of the size relationship, the calcification 64A and the calcification 64B are smaller than 1/10 of the tumor 60A. Therefore, the priorities of the calcification 64A and the calcification 64B are set to be higher than priorities of the other structures of interest. As a result, as illustrated in a lower part of FIG. 11 as an example, the synthesized two-dimensional image created by using the priority is an image in which only the calcification 64A and the calcification 64B are emphasized. In addition, as the closeness relationship, a calcification existing along the mammary gland can also be used.

As described above, in the present embodiment, the priority determined by the priority determination unit 33 is reflected in the tomographic image Dj, and then the synthesized two-dimensional image is created. Therefore, the synthesized two-dimensional image in which the structure of interest having a high priority is emphasized is created. On the other hand, the present disclosure is not limited thereto. For example, first, a synthesized two-dimensional image may be temporarily created without considering the priority. Then, the synthesized two-dimensional image may be processed such that the structure of interest having a higher priority is emphasized, and thus, the final synthesized two-dimensional image may be created. As a method of emphasizing the structure of interest in this form, a form in which only a region of the structure of interest (hereinafter, referred to as an "emphasis target region") is set to have higher brightness as compared with a region around the emphasis target region, a form in which only the emphasis target region is set to a different display state such as blink display or reverse display, a form in which only the emphasis target region is displayed by being surrounded by an external rectangular frame or an external circular frame, and the like can be exemplified.

Figure 12:
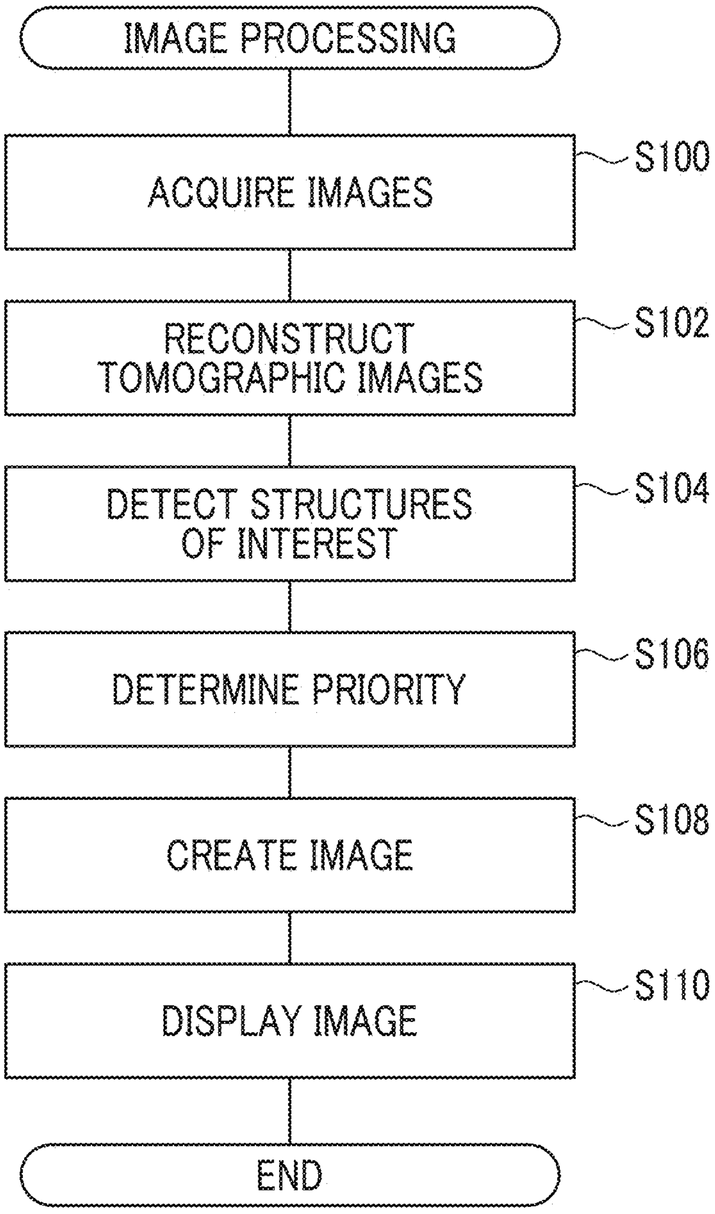
FIG. 12 is a flowchart illustrating an example of image processing according to the embodiment.

Next, processing performed in the present embodiment will be described. FIG. 12 is a flowchart illustrating image processing performed in the present embodiment. It is assumed that a plurality of projection images Gi are acquired in advance and stored in the storage 23. In addition, here, a case where information indicating a type of the structure of interest to be focused and information indicating the mutual relationship are preset will be described.

In a case where the input device 25 receives an instruction to start the processing from the operator, execution of the image processing program 22 is started, and thus, the image processing illustrated in FIG. 12 is started.

First, the image acquisition unit 30 acquires the projection images Gi by reading the projection images Gi from the storage 23, the projection images Gi being obtained by imaging the subject (in the present embodiment, the breast M) with the radiation emitted from the radiation source 16 at a plurality of angles (step S100). Next, the tomographic image reconstruction unit 31 reconstructs the plurality of tomographic images Dj from the acquired projection images Gi (step S102).

Next, the structure-of-interest detection unit 32 detects a plurality of structures of interest from the plurality of reconstructed tomographic images Dj (step S104). Next, the priority determination unit 33 determines a priority for each of the plurality of detected structures of interest having the same type by using the mutual relationship with the other structures of interest (step S106).

In addition, the image creation unit 34 creates a synthesized two-dimensional image from the plurality of tomographic images Dj by using the determined priority (step S108). Subsequently, the display controller 35 displays the synthesized two-dimensional image on the display 24 (step S110), and the processing is ended.

As described above, with the image processing apparatus according to the present embodiment, the projection images obtained by imaging the subject with the radiation at a plurality of angles are acquired, and the plurality of tomographic images are reconstructed from the acquired projection images. The plurality of structures of interest are detected from the plurality of reconstructed tomographic images, and the priority is determined for each of the plurality of detected structures of interest having the same type by using the mutual relationship with the other structures of interest. Therefore, it is possible to determine the superiority and inferiority of the structures of interest having the same type in consideration of the mutual relationship between the structures of interest.

Further, according to the image processing apparatus according to the present embodiment, the synthesized two-dimensional image of the subject is created by using the determined priority. Therefore, it is possible to further improve visibility of the structure of interest in the synthesized two-dimensional image as compared with a case where the determined priority is not used.

In addition, according to the image processing apparatus according to the present embodiment, the mutual relationship is set as at least one of the closeness relationship with other structures of interest in three-dimensional distance or the size relationship with other structures of interest. Therefore, in a case where the closeness relationship is applied as the mutual relationship, it is possible to obtain the priority of the structure of interest to be prioritized from the viewpoint of the closeness relationship, and in a case where the size relationship is applied as the mutual relationship, it is possible to obtain the priority of the structure of interest to be prioritized from the viewpoint of the size relationship.

Further, according to the image processing apparatus according to the present embodiment, at least one type of a calcification, a tumor, a spicula, or a mammary gland is applied as the structure of interest. Therefore, it is possible to determine the superiority and inferiority of the type of the applied structure of interest in consideration of the mutual relationship between the structures of interest.

Further, according to the image processing apparatus according to the present embodiment, the structure of interest is detected by using a machine learning model obtained by performing machine learning in advance, the machine learning model in which information indicating a tomographic image is set as input information and information indicating a plurality of structures of interest is set as output information. Therefore, it is possible to detect the structure of interest with higher accuracy as compared with a case of detecting the structure of interest by performing pattern matching.

Further, in the image processing apparatus according to the present embodiment, an aspect in which the structure of interest is detected by performing pattern matching using a template image of a target structure of interest is adopted. Therefore, according to the aspect, it is possible to more simply detect the structure of interest as compared with a case of detecting the structure of interest by using a machine learning model.

In the embodiment, a case where the CPU 21 provided in the image processing apparatus 4 is applied as the processor according to the technology of the present disclosure has been described. On the other hand, the present disclosure is not limited thereto. For example, the CPU provided in any of the mammography apparatus 1, the console 2, and the image storage system 3 may be applied as a processor according to the technology of the present disclosure.

In addition, in the embodiment, a case where the closeness relationship and the size relationship are each independently applied has been described. On the other hand, the present disclosure is not limited thereto. For example, a form in which the closeness relationship and the size relationship are applied in combination may be used. Examples of this form include a form in which a priority is first determined based on the closeness relationship and then the priority is determined based on the size relationship for a plurality of the structures of interest having the same priority, a form in which, on the contrary, a priority is first determined based on the size relationship and then the priority is determined based on the closeness relationship for a plurality of the structures of interest having the same priority, and the like.

In addition, in the embodiment, the case where the structures of interest are focused on only the calcifications in FIG. 7 to FIG. 11 has been described. However, the present disclosure is not limited thereto. A form in which any one type of a tumor, a spicula, and a mammary gland, or a combination of a plurality of types of structures of interest including a calcification, in addition to a tumor, a spicula, and a mammary gland, is applied as the structure of interest to be focused may be adopted.

In addition, in the embodiment, the case where the relationship, in which the structure of interest having a relatively small size is prioritized, is applied as the size relationship has been described. On the other hand, the present disclosure is not limited thereto. For example, a form in which a relationship in which the structure of interest having a relatively large size is prioritized is applied as the size relationship may be used.

In addition, in the embodiment, the case where the priority having only two stages of priority and non-priority is applied as the priority has been described. On the other hand, the present disclosure is not limited thereto. For example, a form in which a priority having three or more stages is applied as the priority may be used.

In addition, in the embodiment, for example, as hardware structures of processing units that execute various kinds of processing, such as the image acquisition unit 30, the tomographic image reconstruction unit 31, the structure-of-interest detection unit 32, the priority determination unit 33, the image creation unit 34, and the display controller 35, the following various processors can be used. As described above, the various processors include, in addition to the CPU that is a general-purpose processor that executes software (program) to function as various processing units, a programmable logic device (PLD) that is a processor of which a circuit configuration can be changed after manufacture, such as a field programmable gate array (FPGA), and a dedicated electric circuit that is a processor having a circuit configuration that is designed for exclusive use in order to execute a specific process, such as an application specific integrated circuit (ASIC).

One processing unit may be configured by one of the various processors, or may be configured by a combination of the same or different types of two or more processors (for example, a combination of a plurality of FPGAs or a combination of the CPU and the FPGA). In addition, a plurality of processing units may be configured by one processor.

As an example in which the plurality of processing units are configured by one processor, firstly, as represented by a computer such as a client and a server, a form in which one processor is configured by a combination of one or more CPUs and software and the processor functions as the plurality of processing units may be adopted. Secondly, as represented by a system on chip (SoC) or the like, a form in which a processor that implements the function of the entire system including the plurality of processing units by one integrated circuit (IC) chip is used may be adopted. In this way, various processing units are formed using one or more of the above-mentioned various processors as hardware structures.

Further, the hardware structure of these various processors is, more specifically, an electric circuit (circuitry) in which circuit elements such as semiconductor elements are combined.

In addition, in the embodiment described above, the aspect in which the image processing program 22 is stored (installed) in advance in the storage 23 of the image processing apparatus 4 has been described, but the present disclosure is not limited thereto. The image processing program 22 may be provided in a form recorded in a recording medium such as a compact disc read-only memory (CD-ROM), a digital versatile disc read-only memory (DVD-ROM), and a universal serial bus (USB) memory. In addition, the image processing program 22 may be configured to be downloaded from an external device via a network.

From the above description, the invention described in following Appendices can be understood.

APPENDIX 1

An image processing apparatus comprising:

at least one processor, in which the processor is configured to:

acquire projection images obtained by imaging a subject with radiation at a plurality of angles;

reconstruct a plurality of tomographic images from the acquired projection images;

detect a plurality of structures of interest from the plurality of reconstructed tomographic images; and determine a priority for each of the structures of interest having the same type among the plurality of detected structures of interest by using a mutual relationship with other structures of interest.

APPENDIX 2

The image processing apparatus according to Appendix 1, in which the processor is configured to create a synthesized two-dimensional image of the subject by using the determined priority.

APPENDIX 3

The image processing apparatus according to Appendix 1 or 2, in which the mutual relationship is at least one of a closeness relationship with the other structures of interest in a three-dimensional distance or a size relationship with the other structures of interest.

APPENDIX 4

The image processing apparatus according to Appendix 3, in which the mutual relationship is both the closeness relationship and the size relationship.

APPENDIX 5

The image processing apparatus according to any one of Appendixes 1 to 4, in which the structure of interest is at least one type of a calcification, a tumor, a spicula, or a mammary gland.

APPENDIX 6

The image processing apparatus according to any one of Appendixes 1 to 5, in which the processor is configured to detect the structure of interest by using a machine learning model which is obtained by performing machine learning in advance and in which information indicating the tomographic image is set as input information and information indicating the plurality of structures of interest is set as output information.

APPENDIX 7

The image processing apparatus according to any one of Appendixes 1 to 6, wherein the processor is configured to detect the structure of interest by performing pattern matching using a template image of a target structure of interest.

APPENDIX 8

A radiography system comprising:

the image processing apparatus according to Appendix 1; and a mammography apparatus that acquires projection images to be used by the image processing apparatus.

APPENDIX 9

A program causing a computer to execute a process comprising:

acquiring projection images obtained by imaging a subject with radiation at a plurality of angles;

reconstructing a plurality of tomographic images from the acquired projection images;

detecting a plurality of structures of interest from the plurality of reconstructed tomographic images; and determining a priority for each of the structures of interest having the same type among the plurality of detected structures of interest by using a mutual relationship with other structures of interest.

What is claimed is:

1. An image processing apparatus comprising:

at least one processor that is configured to:

acquire projection images obtained by imaging a subject with radiation at a plurality of angles;

reconstruct a plurality of tomographic images from the acquired projection images;

detect a plurality of structures of interest from the plurality of reconstructed tomographic images; and determine a priority for each of the structures of interest having the same type among the plurality of detected structures of interest by using a mutual relationship with other structures of interest, wherein priorities assigned to the structures of interest having the same type are determined such that a priority assigned to one of the structures of interest having the same type is different from a priority assigned to another of the structures of interest having the same type.

2. The image processing apparatus according to claim 1, wherein the at least one processor is configured to create a synthesized two-dimensional image of the subject by using the determined priority.

3. The image processing apparatus according to claim 1, wherein the mutual relationship is at least one of a closeness relationship with the other structures of interest in a three-dimensional distance or a size relationship with the other structures of interest.

4. The image processing apparatus according to claim 3, wherein the mutual relationship is both the closeness relationship and the size relationship.

5. The image processing apparatus according to claim 1, wherein the structure of interest is at least one type of a calcification, a tumor, a spicula, or a mammary gland.

6. The image processing apparatus according to claim 1, wherein the at least one processor is configured to detect the structure of interest by using a machine learning model which is obtained by performing machine learning in advance and in which information indicating the tomographic image is set as input information and information indicating the plurality of structures of interest is set as output information.

7. The image processing apparatus according to claim 1, wherein the at least one processor is configured to detect the structure of interest by performing pattern matching using a template image of a target structure of interest.

8. A radiography system comprising:

the image processing apparatus according to claim 1; and a mammography apparatus that acquires projection images to be used by the image processing apparatus.

9. A non-transitory storage medium storing a program executable by a computer to perform image processing, the image processing comprising:

acquiring projection images obtained by imaging a subject with radiation at a plurality of angles;

reconstructing a plurality of tomographic images from the acquired projection images;

detecting a plurality of structures of interest from the plurality of reconstructed tomographic images; and determining a priority for each of the structures of interest having the same type among the plurality of detected structures of interest by using a mutual relationship with other structures of interest, wherein priorities assigned to the structures of interest having the same type are determined such that a priority assigned to one of the structures of interest having the same type is different from a priority assigned to another of the structures of interest having the same type.

10. A method executed by a computer, the method comprising:

acquiring projection images obtained by imaging a subject with radiation at a plurality of angles;

reconstructing a plurality of tomographic images from the acquired projection images;

detecting a plurality of structures of interest from the plurality of reconstructed tomographic images; and determining a priority for each of the structures of interest having the same type among the plurality of detected structures of interest by using a mutual relationship with other structures of interest, wherein priorities assigned to the structures of interest having the same type are determined such that a priority assigned to one of the structures of interest having the same type is different from a priority assigned to another of the structures of interest having the same type.

* * * * *